United States Patent [19]

Pomponi et al.

[11] Patent Number: 5,217,986
[45] Date of Patent: Jun. 8, 1993

[54] ANTI-ALLERGY AGENT

[75] Inventors: Shirley A. Pomponi, Fort Pierce, Fla.; Vincent P. Gullo, Liberty Corner, N.J.; Ann C. Horan, Summit, N.J.; Mahesh G. Patel, Verona, N.J.; Stephen Coval, Clinton, N.J.

[73] Assignee: Harbor Branch Oceanographic Institution, Inc., Fort Pierce, Fla.

[21] Appl. No.: 858,275

[22] Filed: Mar. 26, 1992

[51] Int. Cl.$^5$ .................. A61K 31/415; C07D 233/64
[52] U.S. Cl. .................... 514/400; 548/336.1
[58] Field of Search ............... 548/342, 336.1; 514/400

[56] References Cited

PUBLICATIONS

Gunasekera et al., Journal of Natural Products, vol. 52, No. 4, pp. 753-756 Jul.-Aug. (1989).
Cimino et al. Tetrahedron Letters, vol. 24, No. 29, pp. 3029-3032, 1983.
Xynas et al, Aust. J. Chem., (1989), 42, 1427-1433.

Primary Examiner—Mary C. Lee
Assistant Examiner—Lenora A. Miltenberger
Attorney, Agent, or Firm—Eric S. Dicker; John Maitner; Matthew Boxer

[57] ABSTRACT

The compound of the formula

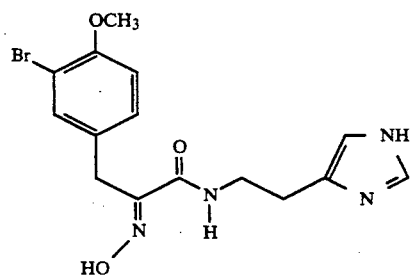

is described. This compound is active in an $H_3$ receptor assay and is an $H_3$ antagonist. Accordingly, the compound of formula I is useful in the treatment of diseases and conditions such as asthma, rhinitis, airway congestion, inflammation, cardiac arrhythmias, hypertension, hyper and hypo motility and acid secretion of the gastrointestinal tract, hypo and hyper activity of the central nervous system (CNS), migraine, and glaucoma.

5 Claims, No Drawings

ANTI-ALLERGY AGENT

BRIEF SUMMARY OF THE INVENTION

The invention relates to the compound of the formula:

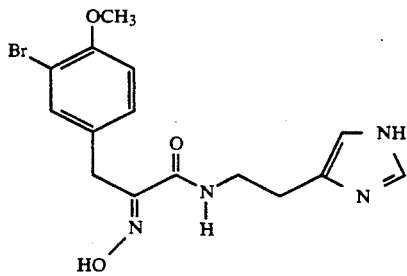

I

The compound of formula I has been given the trivial name verongamine.

The compound of formula I is active in an $H_3$ receptor assay, is an $H_3$ antagonist on guinea pig ileum, and accordingly is useful in the treatment of diseases and conditions such as asthma, rhinitis, airway congestion, inflammation, cardiac arrhythmias, hypertension, hyper and hypo motility and acid secretion of the gastrointestinal tract, hypo and hyper activity of the central nervous system (CNS), migraine, and glaucoma.

The invention also relates to a composition comprising a compound of the formula I and a pharmaceutically acceptable carrier material.

The invention also relates to a method of treating a mammal afflicted with asthma, rhinitis, airway congestion, inflammation, cardiac arrhythmias, hypertension, hyper and hypo motility and acid secretion of the gastrointestinal tract, hypo and hyper activity of the central nervous system (CNS), migraine, and glaucoma which comprises administering an effective amount of a compound of formula I.

The invention also comprises a method for preparing the compound of the formula I by extraction from the marine sponge *Verongula gigantea*.

DETAILED DESCRIPTION OF THE INVENTION

A more complete understanding of the invention can be obtained by reference to the description concerning the preparation of the compound, the compositions and the methods of the invention. It will be apparent to those skilled in the art that the examples involve the use of materials and reagents that are commercially available from known sources, e.g., chemical supply houses, so no details are given respecting them.

The following is a description of the preparation of the compound of formula I. This compound is prepared by extraction from the marine sponge *Verongula gigantea* of the phylum-Porifera, Class-Demospongiae, Order-Verongida, Family-Aplysinidae. A quantity of this sponge was collected at a depth of 210 meters on a flat sand bottom, north of Littel Stirrup Cay, Bahama Islands, and a the coordiates: Latitude—25° 50.68′ N, Longitude—77° 56.74′ W. The specimen (Harbor Branch Oceanographic Institution, Division of Biomedical Marine Research #19-III-87-1-1) was collected using a manned submersible, which was equipped with a color video camera, 7-function manipulator arm, and collection buckets. The sample collected was then frozen and stored in freezers at −10° to −25° C.

The sample, which was not present in abundance at the collection site, was vase-shaped and yellow-purple in color; approximately 25% of the surface was covered with epibionts. A voucher specimen (catalog number 003:00406) is deposited at Harbor Branch Oceanographic Museum, Ft. Pierce, Fla. The voucher specimen is preserved in 70% ethanol with an expected shelf life of at least 30 years and is accessible to those skilled in the art for taxonomic identification purposes.

Descriptions of the marine sponge *Verongula gigantea* can be found in the published literature (e.g. Wiedenmayer, F. 1977. Shallow-water Sponges of the Western Bahamas. Experentia Suppl. 28, pp. 287, Birkhauser Verlag, Basel & Stuttgart). The species is commonly found in the Bahama Islands and Caribbean at depths of 1–10 m. Its morphology is variable and it is described as hollow cylindrical, cup-shaped, vase-shaped, or bowl-shaped. This sample had become dislodged from the substrate and had tumbled into deeper water than it is normally found, however it was still alive at the time of collection.

The extraction process which is set forth below follows FIG. 1.

ISOLATION OF VERONGAMINE

A portion of the frozen sponge (19-III-87-1-1) described above was homogenized with ethanol in a blender, filtered, steeped in ethanol, and filtered. The resulting extracts were combined and concentrated under vacuum to give a brown gum. The gum was partitioned between ethyl acetate and water, and the ethyl acetate fraction subsequently extracted with 5% aqueous hydrochloric acid. After removal of the ethyl acetate layer, the aqueous hydrochloric acid layer was treated with concentrated aqueous sodium hydroxide to adjust the pH to 9. The resulting alkaline solution was extracted with ethyl acetate, and the ethyl acetate extract concentrated under vacuum to give an oily residue.

The residue was chromatographed on silica gel employing gradient elution consisting of 2–20% methanol in dichloromethane. A group of fractions which eluted from approximately 5–15% methanol/dichloromethane, and which displayed $H_3$ activity, were pooled. The residue from these combined fractions was subjected to gel filtration on Sephadex LH-20 with elution by 20:20:1 acetonitrile/dichloromethane/methanol to give pure verongamine. Also obtained is aerophobin-1 which is described in copending case ID 0235 (Ser. No. 07/857,889 filed Mar. 26, 1992).

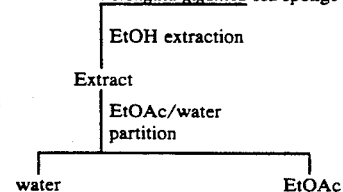

Figure 1. Isolation Scheme

-continued
Figure 1. Isolation Scheme

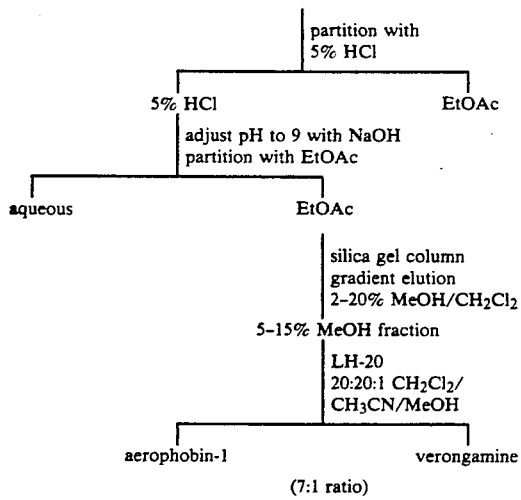

(7:1 ratio)

Verongamine exists as a yellow semi solid oil.

UV (MeOH): $\lambda_{max}$ 388 (630), 289 sh (2660), 280 (3040), 206 (33600).

IR (KBr): cm$^{-1}$ 3390 br, 3231 br, 2936, 2837, 1655, 1495, 1254, 1054.

$^1$H NMR (CD$_3$OD): δ 7.55 br s (1H, H-14), 7.42 d (1H, J=2.1, H-2), 7.17 dd (1H, J=8.4, 2.1, H-6), 6.89 d (1H, J=8.4, H-5), 6.80 br s (1H, H-13), 3.80 s (3H, CH$_3$-15), 3.79 s (2H, CH$_2$-7), 3.47 t (2H, J=7.1, CH$_2$-10), 2.77 t (2H, J=7.1, CH$_2$-11).

$^{13}$C NMR (CD$_3$OD): δ 165.7 s (C-9), 155.9 s (C-4), 153.0 s (C-8), 136.1 d (C-14), 134.8 d (C-2), 131.8 s (C-3), 130.5-d (C-6), 113.1 d (C-5), 112.1 s (C-1), 56.7 q (C-15), 40.3 t (C-10), 28.7 t (C-7), 27.8 t (C-11).

HR FAB MS: observed (M+H)$^+$ peak 381.0573, calculated mass for C$_{15}$H$_{18}$N$_4$O$_3$$^{79}$Br is 381.0562.

FAB MS M/Z (relative intensity): For (M+H)$^+$ 381 (92) and 383 (100) for (M+Na)$^+$ 403 (36) and 405 (38).

Based on the foregoing data, verongamine was assigned the structure shown below. In the structure shown below, the carbon atoms have been numbered to accord with the NMR data shown above.

STRUCTURE OF VERONGAMINE

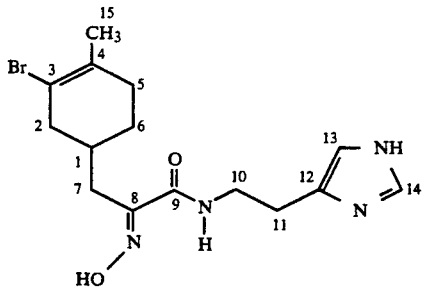

The compound of the invention may form pharmaceutically acceptable salts with organic and inorganic acids. Examples of suitable acids for salt formation are hydrochloric, sulfuric, phosphoric, acetic, citric, malonic, salicyclic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base form differs from the respective salt forms somewhat in certain physical properties, such as solubility in polar solvents, but the salts are otherwise equivalent to the respective free base form and are within the scope of this invention.

The following assay methods were used to illustrate the biological activities of the compound of the invention.

H$_3$ RECEPTOR BINDING ASSAY

The source of the H$_3$ receptors in this experiment was guinea pig brain. The animals used weighed 400–600 g. The tissue was homogenized using a Polytron in a solution of 50 mM Tris, pH 7.5. The final concentration of tissue in the homogenization buffer was 10% w/v. The homogenates were centrifuged at 1000× g for 10 minutes in order to remove clumps of tissue and debris. The resulting supernatants were then centrifuged at 50,000× g for 20 minutes in order to sediment the membranes, which were next washed 3 times in homogenization buffer (50,000× g for 20 minutes each). The membranes were frozen and stored at −70° C. until needed.

The compound to be tested was dissolved in DMSO (dimethyl sulfoxide) and then diluted into the binding buffer (50 mM Tris, pH 7.5) such that the final concentration was 2 μg/mL with 0.1% DMSO. Membranes were then added (400 μg of protein) to the reaction tubes. The reaction was started by the addition of 3 nM [$^3$H]R-α-methylhistamine (8.8 Ci/mmol) and incubated at 30° C. for 30 minutes. Bound ligand was separated from unbound ligand by filtration, and the amount of radioactive ligand bound to the membranes was quantitated by liquid scintillation spectrometry. The incubation was performed in duplicate and the standard error was less than 10%. The compound, which inhibited greater than 50% of the specific binding of radioactive ligand to the receptor, was serially diluted to determine an IC$_{50}$ (in μg/mL).

GUINEA PIG ILEUM ASSAY

Male guinea pigs (450–500 g) were sacrificed by cervical dislocation. Portions of the ileum (20–40 cm) were removed and placed in Tyrodes solution (NaCl, 8.0; KCl, 0.2; MgCl$_2$.6H$_2$O, 0.2; CaCl$_2$, 0.13; NaH$_2$PO$_4$, 0.06; dextrose, 1.0; NaHCO$_3$, 1.0 g/l). The ilea were cut into 2.5 cm segments, mounted between platinum wire coaxial electrodes and placed in water-jacketed organ baths containing 25 ml of the Tyrodes solution. Bath fluid temperature was maintained at 37° C. and aerated with 95% 0$_2$-5% CO$_2$. The muscles were suspended from isometric force transducers (Grass FT03C) under 0.3 g resting tension. Contractions were amplified on a Buxco tension monitor and recorded on a Harvard polygraph. Monophasic rectangular-wave electrical pulses were delivered to the tissues every 60 seconds. The ileum segments were maximally stimulated with 3 volts at 40 Hz frequency and 1 mseconds duration in 1 pulse train every 60 seconds. The duration of 1 msecond was then decreased by 0.1 msecond and until the size of the contraction reached 80% of the maximal response. Once this 80% response was determined it was evoked every 60 seconds throughout the experiment. All experiments were conducted with 1 μM of chlorpheniramine present in the Tyrodes buffer.

Rα-methylhistamine inhibits the electrical field stimulated contractions of the guinea pig ileum and was used as the H3 agonist reference standard. H3 agonists were studied for their ability to inhibit the electrical field stimulated contractions and their activity was expressed as a percentage of the maximum Rα-methylhistamine effect. Agonists were tested by addition of logarithmically increasing doses to the bath fluid at intervals of 1 minute. Thioperamide is a competitive inhibitor of Rα-methylhistamine activity and was used as the H3 antagonist reference standard. Antagonists were tested for their ability to inhibit Rα-methylhistamine and were added to the bath 5 minutes before generating an Rα-methylhistamine concentration-response curve.

Relative potency for agonists was determined from the pD2 (Furchgott, R. F., The pharmacology of Vascular Smooth Muscle. Pharm. Rev. 7, 183, 1955.) calculations. Relative potency for antagonists was determined from pA2 calculations. (See Furchgott above).

| Results | | |
|---|---|---|
| Compound | H3 receptor Binding IC50 | Guinea Pig Ileum |
| verongamine | 0.19 μg/mL | antagonist @ 1 μg/mL |

Based on the foregoing biological data, it can be concluded that the compound of formula I is an H3 receptor antagonist, and accordingly is useful in the treatment of diseases and conditions such as asthma, rhinitis, airway congestion, inflammation, cardiac arrhythmias, hypertension, hyper and hypo motility and acid secretion of the gastrointestinal tract, hypo and hyper activity of the central nervous system (CNS), migraine, and glaucoma.

In accordance with the invention, pharmaceutical compositions comprise, as the active ingredient, an effective amount of the new compound of formula I and one or more non-toxic pharmaceutically acceptable carriers or diluents. Examples of such carriers for use in the invention include ethanol, dimethyl sulfoxide, glycerol, silica, alumina, starch equivalent carriers and diluents.

While effective amounts may vary, as conditions in which such compositions are used vary, a minimal dosage required for therapeutic activity is generally between 1 and 1000 milligrams, one to four times daily. The compound of the invention may be administered as a tablet, a solution, a capsule, a suspension or an aerosol. It may be administered orally, subcutaneously, intravenously, topically or by inhalation.

Therapeutic application of the compound of formula I and compositions containing it, can be contemplated to be accomplished by any suitable therapeutic method and technique presently or prospectively known to those skilled in the art.

What is claimed is:

1. The compound verongamine of the formula

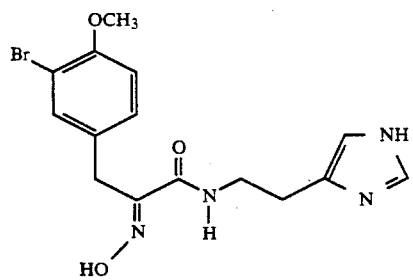

or a pharmaceutically acceptable salt thereof.

2. A pharmaceutical composition comprising an effective amount of the compound of claim 1 and a pharmaceutically acceptable carrier material.

3. A method for treating a mammal afflicted with asthma, rhinitis, airway congestion, inflammation, cardiac arrhythmia, hypertension, hyper and hypo motility and acid secretion of the gastrointestinal tract, hypo and hyper activity of the central nervous system (CNS), migraine, or glaucoma which comprises administering an effective amount of the compound of claim 1.

4. The compound verongamine, effective in inhibiting H3 receptors, obtained from the marine sponge, *Verongula gigantea*
by the extraction process set forth in FIG. 1 just below,

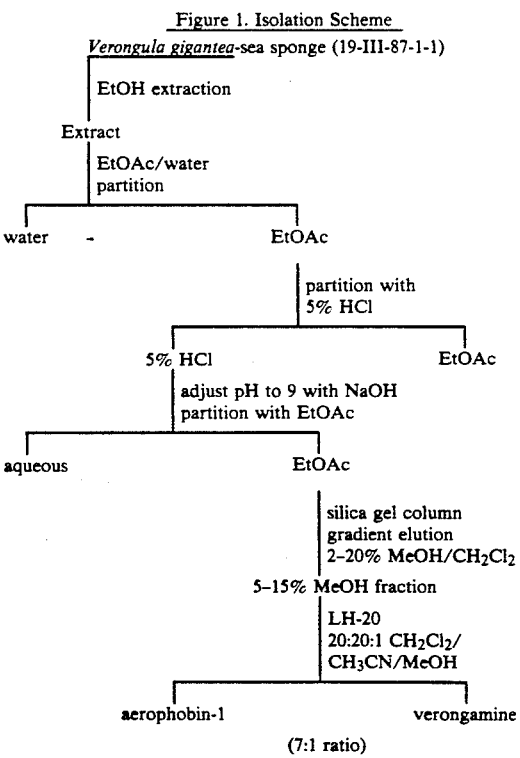

being a yellow semi solid oil; UV (MeOH): λ$_{max}$ 388 (630), 289 sh (2660), 280 (3040), 206 (33600); IR (KBr): cm$^{-1}$ 3390 br, 3231 br, 2936, 2837, 1655, 1495, 1254, 1054, $^1$H NMR (CD$_3$OD): δ 7.55 br s (1H, H-14), 7.42 d (1H, J=2.1, H-2), 7.17 dd (1H, J=8.4, 2.1, H-6), 6.89 d (1H, J=8.4, H-5), 6.80 br s (1H, H-13), 3.80 s (3H, CH$_3$-15), 3.79 s (2H, CH$_2$-7), 3.47 t (2H, J=7.1, CH$_2$-10), 2.77 t (2H, J=7.1, CH$_2$-11); $^{13}$C NMR (CD$_3$OD): δ 165.7 s (C-9), 155.9 s (C-4), 153.0 s (C-8), 136.1 d (C-14), 134.8 d (C-2), 131.8 s (C-3), 130.5-d (C-6), 113.1 d (C-5), 112.1 s (C-1), 56.7 q (C-15), 40.3 t (C-10), 28.7 t (C-7), 27.8 t (C-11); HR FAB MS: observed (M+H)$^+$ peak 381.0573, calculated mass for C$_{15}$H$_{18}$N$_4$O$_3$$^{79}$Br is 381.0562; FAB MS M/Z (relative intensity): for (M+H)$^+$ 381 (92) and 383 (100) for (M+Na)$^+$ 403 (36) and 405 (38).

5. A method for preparing the compound verongamine of the formula

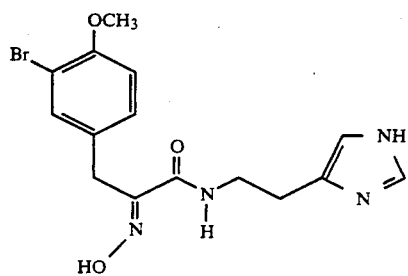

I which comprises extracting the marine sponge, *Verongula gigantea*, by the process of FIG. 1 just below

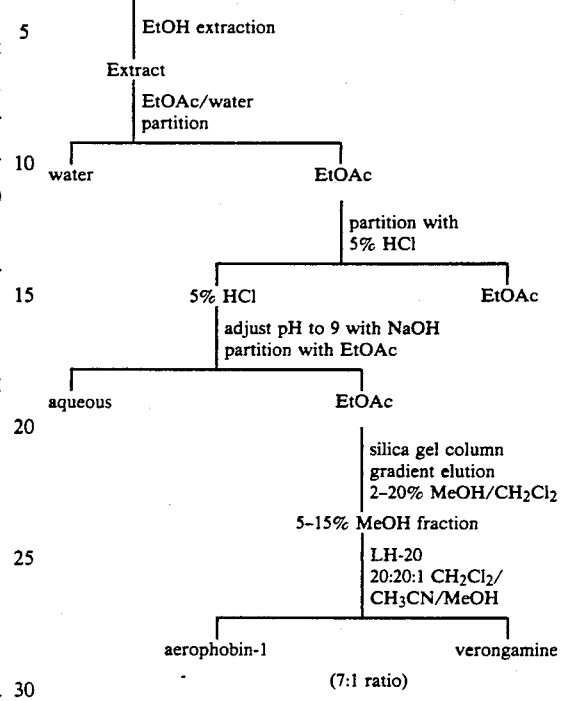

Figure 1. Isolation Scheme
*Verongula gigantea*-sea sponge (19-III-87-1-1)

* * * * *

UNITED STATES PATENT AND TRADEMARK OFFICE
CERTIFICATE OF CORRECTION

PATENT NO. : 5,217,986  Page 1 of 2
DATED : June 8, 1993
INVENTOR(S) : Shirley A. Pomponi, Vincent P. Gullo, Ann C. Horan, Mahesh G. Patel, Stephen Coval It is certified that error appears in the above-indentified patent and that said Letters Patent is hereby corrected as shown below:

Column 1: line 63: "a the coordinates" should read --at the coordinates--.
Column 3: lines 45-52:

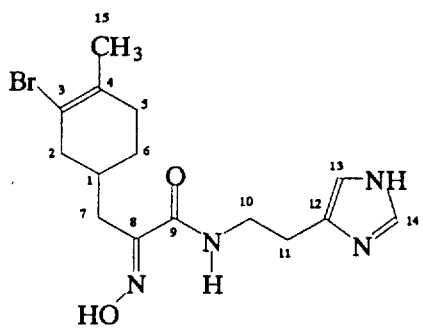

should read

UNITED STATES PATENT AND TRADEMARK OFFICE
CERTIFICATE OF CORRECTION

PATENT NO. : 5,217,986

DATED : June 8, 1993

INVENTOR(S) : Shirley A. Pomponi, Vincent P. Gullo, Ann C. Horan, Mahesh G. Patel, Stephen Coval It is certified that error appears in the above-indentified patent and that said Letters Patent is hereby corrected as shown below:

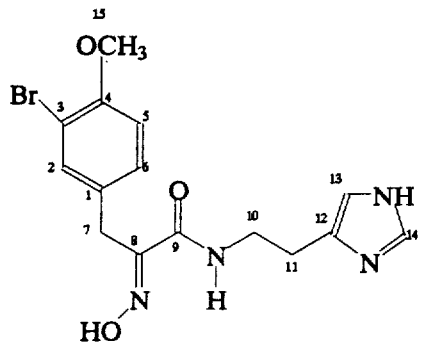

Column 3: line 63: "salicyclic" should read --salicylic--.

Column 5: line 45: "non-toxic" should read --non-toxic,--.

Signed and Sealed this

Twenty-first Day of June, 1994

Attest:

BRUCE LEHMAN

*Attesting Officer*   *Commissioner of Patents and Trademarks*